US00PP30481P2

(12) United States Plant Patent
Van Swieten

(10) Patent No.: US PP30,481 P2
(45) Date of Patent: May 7, 2019

(54) ***PHALAENOPSIS* ORCHID PLANT NAMED 'PHALFUSBI'**

(50) Latin Name: ***Phalaenopsis* hybrid**
Varietal Denomination: PHALFUSBI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,156

(22) Filed: Feb. 13, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALFUSBI', particularly characterized by having light red-purple flowers with an orange lip, 1 to 2 peduncles that are medium long and sturdy, leaves that are oblong, and is propagated by meristem tissue culture, is disclosed.

3 Drawing Sheets

Genus and species: *Phalaenopsis* hybrid.
Variety denomination: 'PHALFUSBI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFUSBI'.

The new *Phalaenopsis* plant is a product of a planned breeding program conducted by the inventor in Bleiswijk, The Netherlands. The objective of this breeding program was to create a new *Phalaenopsis* plant with numerous attractive and unique, light red-purple flowers with an orange lip, suitable for potted plant production.

The new *Phalaenopsis* plant 'PHALFUSBI' is a result of cross-pollination made by the inventor in October 2007 in Bleiswijk, The Netherlands of the proprietary female, or seed parent, *Phalaenopsis* hybrid '21067-0002' (unpatented) with the proprietary male, or pollen parent, *Phalaenopsis* hybrid '23090-01' (unpatented).

The new *Phalaenopsis* was selected by the inventor as a single plant within the progeny of the stated cross-pollination in a controlled greenhouse in Bleiswijk, The Netherlands in October 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

'PHALFUSBI' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFUSBI' as a new and distinct variety of *Phalaenopsis* plant.

1) Light red-purple flowers with an orange lip;
2) 1 to 2 peduncles;
3) Peduncle is medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, bud and foliage of the plant; the colors shown are as true as can be reasonably obtained by conventional photographic procedures. The photographs were taken in a greenhouse in Bleiswijk, The Netherlands, from 50-week old plants in December 2017. Colors in the photographs may differ from the color values cited in the detailed botanical description, which accurately describe the actual colors of the new variety.

DESCRIPTION OF THE NEW VARIETY

Figure 1:
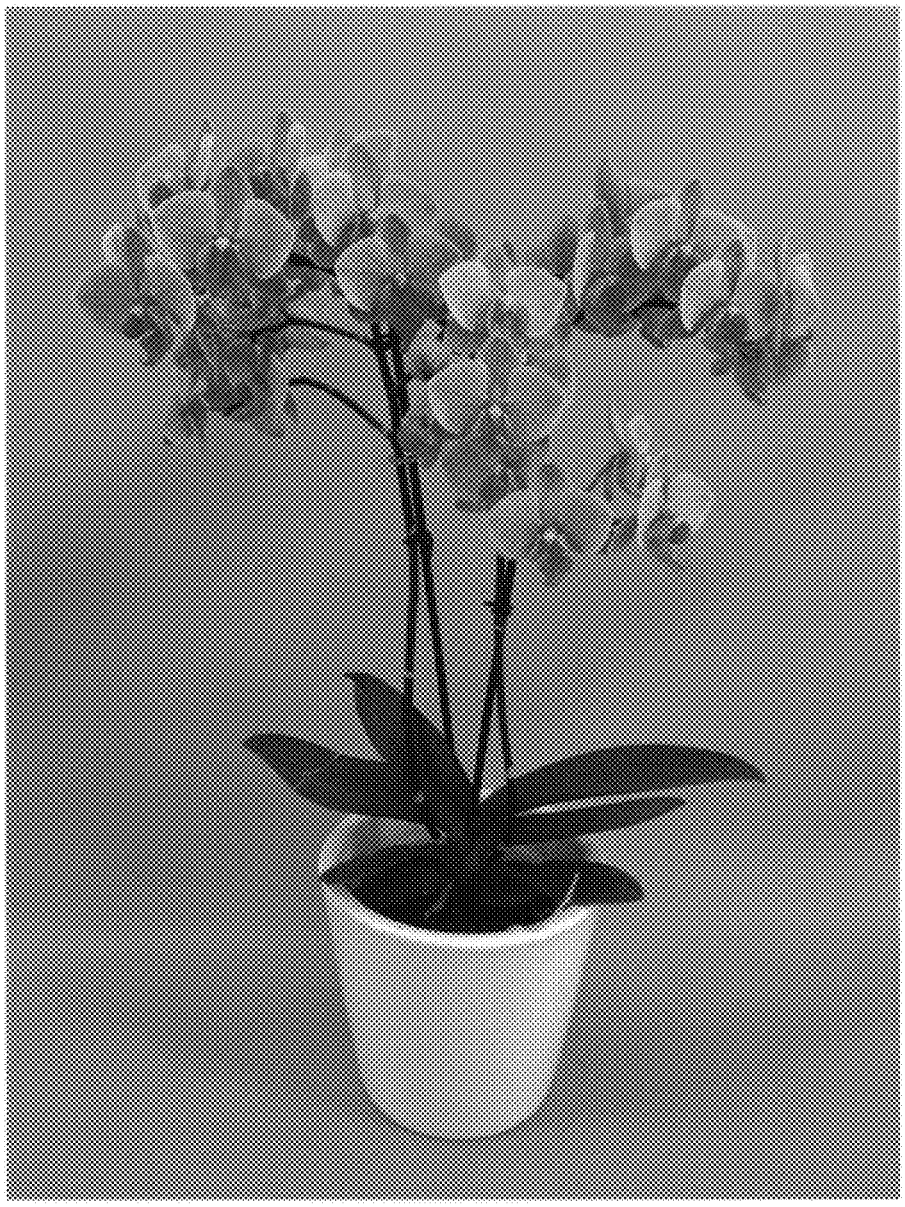
FIG. 1 shows the overall plant habit, including blooms, bud and foliage of 'PHALFUSBI'.
Figure 2:
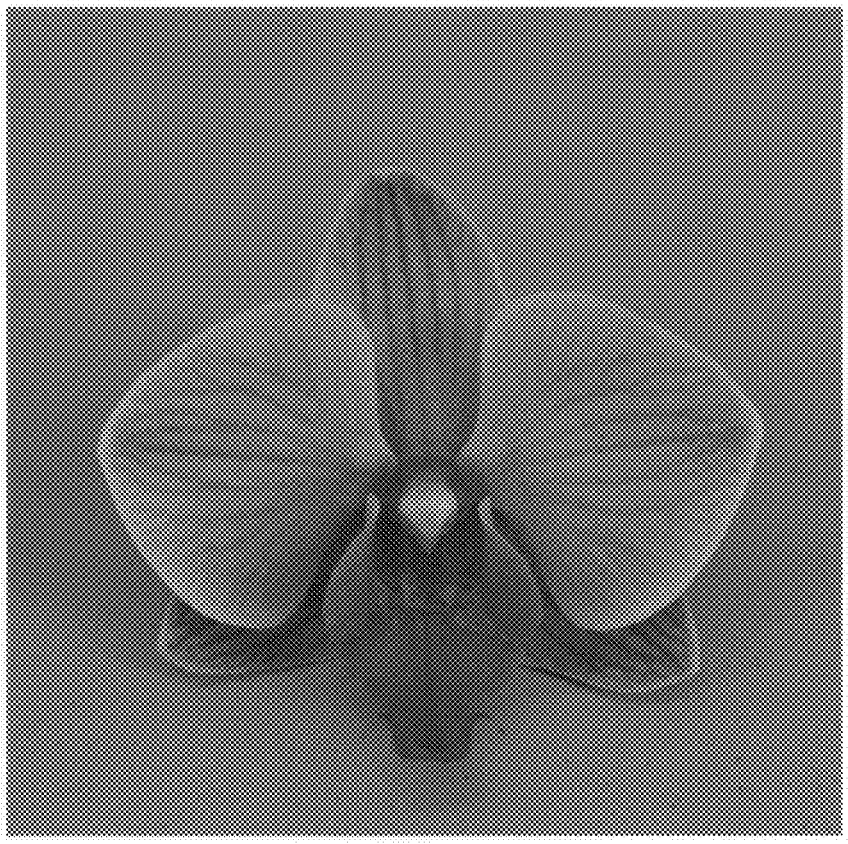
FIG. 2 shows a close-up of a flower of 'PHALFUSBI'.
Figure 3:
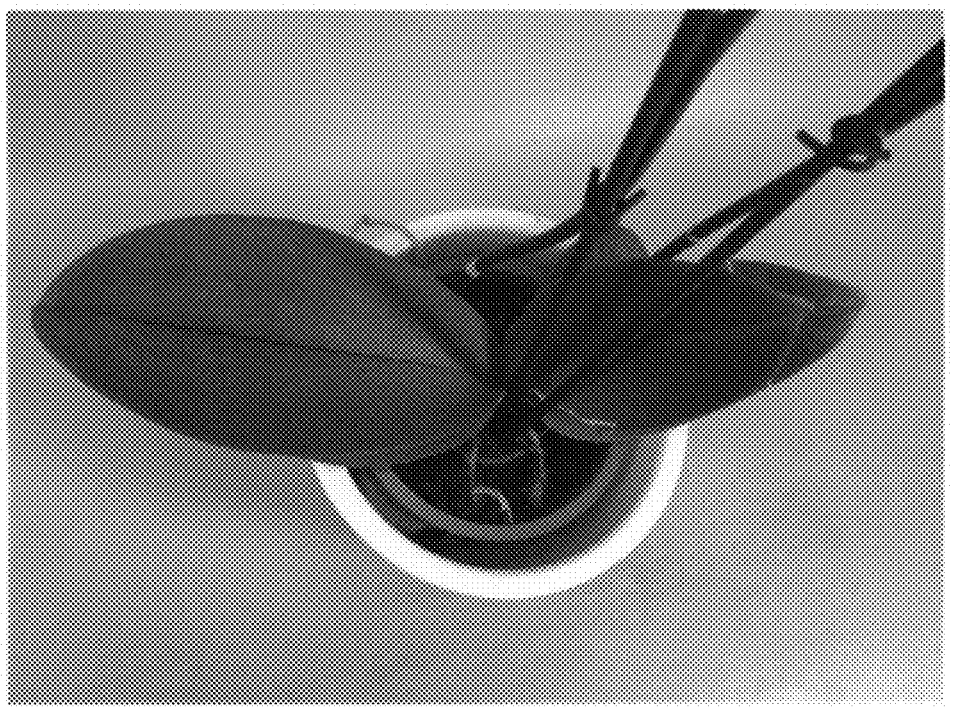
FIG. 3 shows an overhead view of the leaves of 'PHALFUSBI'.

The following detailed description sets forth the distinctive characteristics of 'PHALFUSBI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in December 2017 on flowering plants which were planted in 9 centimeter (diameter) pots. After in-vitro propagation, the plants were grown in nursery trays for 18-20 weeks, followed by transplantation to 9 centimeter (diameter) pots and grown in a greenhouse between 27° C. to 29° C. for 25 weeks, continued by a cooling period of 6 weeks between 18° C. to 20° C. and 11 weeks in a greenhouse of 21° C. Flowering occurs after 42-weeks in a 9 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFUSBI'.

Parentage:

*Female parent*.—*Phalaenopsis* cultivar '21067-0002' (unpatented).

*Male parent*.—*Phalaenopsis* cultivar '23090-01' (unpatented).

Propagation:

*Type*.—Meristem tissue culture.

Roots:

*Root description*.—Greyed-green colored roots (between RHS 190B and 190C) with branching lateral roots having light green (RHS 147D) colored root tips.

Plant:

*Commercial crop time to flowering*.—Following asexual propagation (in-vitro), the rooted cuttings grow for 18-20 weeks. After transplantation in 9 cm pots, the plants are finished after 40 to 42 weeks.

*Growth habit of peduncle*.—Upright to slightly pendant.

*Height* (*from soil level to top of inflorescence*).—Approximately 35.0 cm to 40.0 cm.

*Width* (*measured from leaf tips*).—About 29.0 cm to 31.0 cm.

*Vigor*.—Moderate.

Leaves:

*Mature leaves*.—Quantity per plant: 7 to 9 leaves are produced before flowering. Arrangement: Alternate on the stem, folded lengthwise along the center (plicate). Attachment: Leaves are directly attached to the stem. Length (fully expanded): 15.0 cm to 17.0 cm. Width: 7.5 cm to 8.5 cm. Shape: Oblong. Base shape: Moderately elongated. Apex: Obtuse to rounded unequal. Leaf blade angle with the petiole (measured from the horizontal position): Between 25 degrees and 35 degrees. Leaf margin: Entire. Color: Upper surface: RHS 146A with silver glow (RHS 194A). Lower surface: RHS 146B. Texture: Rough. Thickness: 2.0 mm to 2.3 mm. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—18 to 25.

*Length*.—35.0 cm to 40.0 cm.

*Diameter*.—3.9 mm to 4.2 mm.

*Strength*.—Moderate.

*Aspect*.—Upright to slightly pendant.

*Texture*.—Smooth.

*Color*.—Mix of brown (RHS 200A) and light green (RHS 147C).

*Internode length*.—3.0 cm to 4.0 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 170.0 mm to 190.0 mm.

*Flowering time*.—First flowers can be expected 7 to 8 months after planting in a 9 cm (diameter) pot.

*Flower*.—Height: 50.0 mm to 52.0 mm. Diameter: 58.0 mm to 60.0 mm. Depth of lip: 16.0 mm to 18.0 mm. Shape in lateral view: Concave. Rate of opening: Fully opened about 2-3 days after petal separation. Orientation at opening: Slanted upward and outward. Number of petals per flower: Three. Number of sepals per flower: Three.

*Flower longevity*.—On the plant: 11 to 16 weeks.

*Fragrance*.—Absent.

*Flower bud*.—Average size: Medium. Length: 15.0 mm to 17.0 mm. Width: 13.0 mm to 15.0 mm. Shape: Egg shaped. Color: Light greyed-green (RHS 146D), red-purple (RHS 72A) and light purple (RHS 77D).

*Petals*.—Arrangement: Open/free. Shape: Semi-circular. Apex: Obtuse asymmetric. Margin: Slightly undulated. Length (from base to tip): 20.0 mm to 22.0 mm. Width: 30.0 mm to 32.0 mm. Color (when fully opened): Upper surface: Basic color: Light red-purple (RHS N78D). Over color: Red-purple (RHS N78A) at the base; pink-purple (RHS N78C) stripes. Lower surface: Basic color: Light purple (RHS 76B). Over color: Light purple (RHS 77D); pink-purple (RHS N78C) stripes.

*Dorsal sepal*.—Shape: Elliptic. Apex: Obtuse symmetric. Margin: Entire. Length (from base to tip): 27.0 mm to 29.0 mm. Width: 20.0 mm to 22.0 mm. Texture (both upper and lower surfaces): Smooth and satiny. Color (when fully opened): Upper surface: Basic color: Light red-purple (RHS N78D). Over color: Red-purple (RHS N78B) at the base and purple-pink (RHS N78C) stripes. Lower surface: Basic color: Light purple (RHS 77D). Over color: Red-purple (RHS N78B) stripes.

*Lateral sepals*.—Shape: Ovate. Apex: Obtuse asymmetric. Margin: Entire. Length (from base to tip): 27.0 mm to 29.0 mm. Width: 20.0 mm to 22.0 mm. Texture (both upper and lower surfaces): Smooth and satiny. Color (when fully opened): Upper surface: Basic color: Light red-purple (RHS N78D). Over color: Light green (RHS 145C) at the base and red-orange (between RHS 181C and 181D) with small red-purple (RHS 61A) dots and red-purple (RHS N78B) stripes. Lower surface: Basic color: Light purple (RHS 77D). Over color: Light green (RHS 146D) at the base and red-purple (RHS N78B) toward the tip.

*Labellum* (*lip*).—Texture (both upper and lower surfaces): Smooth and satiny. Shape: Not clearly describable. Whiskers: Present. Length of whiskers:

7.0 mm to 9.0 mm. Color of whiskers: Dark red-orange (RHS 178B). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Slightly undulated. Length: 13.0 mm to 15.0 mm. Width: 8.0 mm to 10.0 mm. Texture (both upper and lower surfaces): Smooth and satiny. Color: Light yellow (RHS 10B) with few red-orange (RHS 178C) stripes at the base; orange (RHS 167A) and red-orange (RHS 178C) toward the margin.

*Apical lobe*.—Shape: Triangular. Margin: Entire. Length: 15.0 mm to 17.0 mm. Width: 14.0 mm to 16.0 mm. Texture (both upper and lower surfaces): Smooth and satiny. Color: Yellow (RHS 13A) at the base; orange (between RHS 178C and 178D) toward the whiskers.

*Callus*.—Average size: Small to medium. Height: 5.0 mm to 6.0 mm. Length: 4.0 mm to 5.0 mm. Width: 3.0 mm to 4.0 mm. Color: Yellow (RHS 14A), dotted (RHS 60A).

Reproductive organs:

*Column*.—Length: 8.0 mm to 10.0 mm. Diameter: 4.6 mm to 4.8 mm. Color: Red-purple (RHS N78B).

*Pollinia*.—Quantity: 2. Diameter: 1.0 mm to 1.1 mm. Color: Orange (RHS 24A).

*Ovary*.—Length: 10.0 mm to 12.0 mm. Diameter: 1.7 mm to 1.9 mm. Color: Purplish-pink (RHS N78C).

*Pedicel*.—Length: 32.0 mm to 34.0 mm. Diameter: 2.0 mm to 2.2 mm. Texture: Smooth. Color: Light green (RHS 195B) and light red-purple (RHS N78D) at the base; light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

Temperature tolerance: Tolerant to a low temperature of about 15° C. and to a high temperature of about 30° C.

COMPARISON WITH PARENTAL LINES AND MOST SIMILAR VARIETIES

'PHALFUSBI' differs from female parent plant '21067-0002' (unpatented) in that 'PHALFUSBI' has smaller flowers and longer whiskers than '21067-0002'.

'PHALFUSBI' differs from male parent plant '23090-01' (unpatented) in that 'PHALFUSBI' has triangular apical lobes that are orange toward the whiskers, whereas '23090-01' has circular apical lobes that are orange-brown and red toward the whiskers. Additionally, 'PHALFUSBI' has larger flowers and longer whiskers than '23090-01'.

'PHALFUSBI' is most similar to the commercial *Phalaenopsis* plants named 'PHALCRAZOH' (unpatented) and 'PHALBARBOK' (unpatented). 'PHALFUSBI' differs from the commercial variety 'PHALCRAZOH' in that 'PHALFUSBI' has light red-purple flowers, apical lobes that are mainly orange, and leaves with over color, whereas 'PHALCRAZOH' has light purple flowers, apical lobes that are mainly pink, and leaves without over color. Additionally, 'PHALFUSBI' has larger flowers and longer whiskers than 'PHALCRAZOH'.

'PHALFUSBI' differs from the commercial variety 'PHALBARBOK' in that 'PHALFUSBI' has light red-purple flowers, apical lobes that are mainly orange, and leaves with over color, whereas 'PHALBARBOK' has light purple flowers, apical lobes that are mainly very light pink, and leaves without over color. Additionally, 'PHALFUSBI' has smaller flowers and shorter whiskers than 'PHALBARBOK'.

I claim:

1. A new and distinct variety of *Phalaenopsis* plant named 'PHALFUSBI', substantially as described and illustrated herein.

* * * * *